US007763638B2

(12) United States Patent
Aissaoui et al.

(10) Patent No.: US 7,763,638 B2
(45) Date of Patent: Jul. 27, 2010

(54) SUBSTITUTED 1,2,3,4-TETRAHYDROISOQUINOLINE DERIVATIVES

(75) Inventors: Hamed Aissaoui, Pulversheim (FR); Martine Clozel, Binningen (FR); Walter Fischli, Allschwil (CH); Ralf Koberstein, Lörrach (DE); Thomas Weller, Binningen (CH)

(73) Assignee: Actelion Pharmaceuticals Ltd., Allschwill (CH)

( * ) Notice: Subject to any disclaimer, the term of this patent is extended or adjusted under 35 U.S.C. 154(b) by 884 days.

(21) Appl. No.: 10/598,449

(22) PCT Filed: Feb. 23, 2005

(86) PCT No.: PCT/EP2005/001879

§ 371 (c)(1),
(2), (4) Date: Aug. 30, 2006

(87) PCT Pub. No.: WO2005/118548

PCT Pub. Date: Dec. 15, 2005

(65) Prior Publication Data
US 2007/0191424 A1    Aug. 16, 2007

(30) Foreign Application Priority Data
Mar. 1, 2004    (EP)    ................ PCT/EP2004/002020

(51) Int. Cl.
C07D 217/18    (2006.01)
A61K 31/47    (2006.01)
(52) U.S. Cl. ........................................ 514/310; 546/146
(58) Field of Classification Search ........................ None
See application file for complete search history.

(56) References Cited
U.S. PATENT DOCUMENTS

| 3,480,714 | A | 11/1969 | Werner |
| 6,703,392 | B2 | 3/2004 | Aissaoui et al. |
| 7,192,950 | B2 | 3/2007 | Aissaoui et al. |
| 2009/0082394 | A1 | 3/2009 | Jenck |

FOREIGN PATENT DOCUMENTS

| DD | 204917 | 12/1983 |
| DD | 258817 | 8/1988 |
| DD | 261158 | 10/1988 |
| EP | 0494623 | 7/1992 |
| EP | WO-01/85693 A1 | 11/2001 |
| JP | 61 053268 | 3/1986 |
| JP | 07 267961 | 10/1995 |
| JP | 10 095766 | 4/1998 |
| WO | WO-97/20789 | 6/1997 |
| WO | WO98/05352 | 2/1998 |
| WO | WO98/23593 | 6/1998 |
| WO | WO-99/09024 A1 | 2/1999 |
| WO | WO99/58533 | 11/1999 |
| WO | WO00/29399 | 5/2000 |
| WO | WO00/35882 | 6/2000 |
| WO | WO00/47284 | 8/2000 |
| WO | WO-00/47576 A1 | 8/2000 |
| WO | WO00/47577 | 8/2000 |
| WO | WO-00/47580 A2 | 8/2000 |
| WO | WO00/78742 | 12/2000 |
| WO | WO00/78744 | 12/2000 |
| WO | WO01/02368 | 1/2001 |
| WO | WO01/08720 | 2/2001 |
| WO | WO01/14555 | 3/2001 |
| WO | WO01/30991 | 5/2001 |
| WO | WO01/40259 | 6/2001 |
| WO | WO01/40304 | 6/2001 |
| WO | WO01/42268 | 6/2001 |
| WO | WO-01/68609 A | 9/2001 |
| WO | WO01/74162 | 10/2001 |
| WO | WO-01/96302 A1 | 12/2001 |
| WO | WO-02/44172 A1 | 6/2002 |
| WO | WO-02/051838 A | 7/2002 |
| WO | WO02/087606 | 11/2002 |
| WO | WO02/089800 | 11/2002 |
| WO | WO-02/090355 A1 | 11/2002 |
| WO | WO-03/002559 A2 | 1/2003 |
| WO | WO-03/002561 A1 | 1/2003 |
| WO | WO03/032991 | 4/2003 |
| WO | WO03/037847 | 5/2003 |
| WO | WO03/041711 | 5/2003 |
| WO | WO03/051368 | 6/2003 |
| WO | WO03/051871 | 6/2003 |
| WO | WO03/051872 | 6/2003 |
| WO | WO03/051873 | 6/2003 |
| WO | WO03/091219 | 11/2003 |
| WO | WO2004/019881 | 3/2004 |
| WO | WO2004/026866 | 4/2004 |

(Continued)

OTHER PUBLICATIONS

Jaeger et al., Effects of Orexin-A on Memory Processing, Peptides, 23 (2003), 1683-1688.

(Continued)

Primary Examiner—Zinna N Davis
(74) Attorney, Agent, or Firm—Hoxie & Associates LLC

(57) ABSTRACT

The invention relates to novel 1,2,3,4-tetrahydroisoquinoline derivatives and their use as active ingredients in the preparation of pharmaceutical compositions. The invention also concerns related aspects including processes for the preparation of the compounds, pharmaceutical compositions containing one or more of those compounds and methods of treatment comprising administration of said compounds to a mammal.

6 Claims, No Drawings

FOREIGN PATENT DOCUMENTS

| | | |
|---|---|---|
| WO | WO2004/041791 | 5/2004 |
| WO | WO2004/041807 | 5/2004 |
| WO | WO2004/041816 | 5/2004 |
| WO | WO2004/052876 | 6/2004 |
| WO | WO2004/054510 | 7/2004 |
| WO | WO-2004/085403 A | 10/2004 |
| WO | WO2007/105177 | 9/2007 |
| WO | WO2007/122591 | 11/2007 |

OTHER PUBLICATIONS

Hutchins et al., Solid Phase Synthesis of Tetrahydroisoquinolines & Tetrahydroimidazopyridines, Tetrahedron Letters (1996), 37, 4865-4868.
Stahl et al., Handbook of Pharmaceutical Salts, Wiley-VCH, Weinheim, Zurich (2002), 329-350.
Telegdy et al., Regulatory Peptides, 104 (2002), 105-110.
Van Del Pol et al., J. Physiol. (2002), 541(1), 169-185.
Sakurai, T. et al.; "Orexins and Orexin Receptors: A Family of Hypothalamic Neuropeptides and G Protein-Coupled Receptors that Regulate Feeding Behavior"; Cell, vol. 92, pp. 573-585, Feb. 20, 1998.
Chemelli, R. et al.; "Narcolepsy in *orexin* Knockout Mice: Molecular Genetics of Sleep Regulation"; Cell, vol. 98, pp. 437-451, Aug. 20, 1999.
Koberstein, R. et al.; "Tetrahydroisoquinolines as Orexin Receptor Antagonists: Strategies for Lead Optimization by Solution-Phase Chemistry"; Chimia 57 (2003), pp. 270-275.
Gould, P.; "Salt selection for basic drugs"; International Journal of Pharmaceutics; 33 (1986), pp. 201-217.
Remington: The Science and Practice of Pharmacy, 20th Edition, 2001, Marck Publishing Company, Easton, Pennsylvania.
Uematsu, N. et al.; "Asymmetric Transfer Hydrogenation of Imines"; J. Am. Chem. Soc. 1996, 118, pp. 4916-4917.
Sakurai T. The neural circuit of orexin (hypocretin): maintaining sleep and wakefulness. Nature Reviews. Neuroscience, vol. 8; Mar. 2007.
Sutcliffe J.G. & De Lecea L. The hypocretins: setting the arousal threshold. Nature Reviews. Neuroscience 3, 339-49; 2002.
Brisbare-Roch C, Feletti L, Koberstein R, Nayler O, Jenck F. Transient orexin receptor blockade induces sleep without cataplexy in rats, Nature Clinical Practice Neurology, May 2007, vol. 3, No. 5, p. 245.
Jenck F, Fischer C, Qiu C, Hess P, Koberstein R, Brisbare-Roch C Somnolence induced by pharmacological blockade of both orexin OX1 and OX2 receptors in dogs, Sleep and Biological rhythms 2007,5, (S1), A79 Poster 271 at the World Sleep Congress, Cairns, Sep. 2007.
Official Note 34103 of Instituto Mexicano de la Propriedad Industrial, dated Apr. 28, 2009 in Mexican Patent No. 269553, PA/a/2006/009833, foreign counterpart to present application, Actelion Pharmaceutical LTD.
Response of Jun. 25, 2009 to Official Note 34103 of Instituto Mexicano de la Propriedad Industrial, dated Apr. 28, 2009 in Mexican Patent No. 269553, PA/a/2006/009833, foreign counterpart to present application, Actelion Pharmaceutical LTD.
Hoever P, De Haas S, Winkler J, Cavallaro M, Van Gerven J, Dingemanse J, Entry-into-humans study with almorexant (ACT-078573), a dual orexin receptor antagonist: tolerability, safety, and pharmacokinetics, Sleep and Biological rhythms 2007,5 (S1): A131, Poster 444 at the World Sleep Congress, Cairns, Sep. 2007.
Hoever P, De Haas S, Chiossi E, Van Gerven J, Dingemanse J, Entry-into-humans study with almorexant (ACT-078573), a dual orexin receptor antagonist: pharmacodynamics, Sleep and Biological rhythms 2007,5 (S1): A131, Poster 443 at the World Sleep Congress, Cairns, Sep. 2007.
Dingemanse J, Dorffner G, Hajak G, Benes H, Danker-Hopfe H, Polo O, Saletu B, Barbanoj MJ, Pillar G, Penzel T, Chiossi E, Hoever P, Proof-of-concept study in primary insomnia patients with almorexant (ACT-078573), a dual orexin receptor antagonist, Sleep and Biological rhythms 2007,5: A194, Poster 653 at the World Sleep Congress, Cairns, Sep. 2007.
Brisbare-Roch C, Dingemanse J, Koberstein R, Hoever P, Aissaoui H, Flores S, Mueller C, Nayler O, Vangerven J, Dehaas S, Hess P, Qiu C, Buchmann S, Scherz M, Weller T, Fischli W, Clozel M & Jenck F, Promotion of sleep by targeting the orexin system in rats, dogs and humans, Nature Medicine, 13: 150-155, 2007.
Jenckf, Brisbare-Roch C, Flores S, Koberstein R, Nayler O, Dingemanse J, Clozel M, Correspondence on "promotion of sleep by targeting the orexin system in rats, dogs and humans", Nature Medicine, 13: 525-526, 2007.
Brisbare-Roch C, Clozel M, Jenck F, Effects of repeated oral administration of the orexin receptor antagonist almorexant in male rats and dogs, Sleep 2008,31: A38 Poster 0118 at the US Associated Professional Sleep Societies meeting, Baltimore, Jun. 2008.
Hoever P, De Haas S, Chiossi E, Van Gerven J, Dingemanse J, Multiple-dose pharmacokinetics, pharmacodynamics, safety, and tolerability of the orexin receptor antagonist almorexant in healthy subjects. Sleep 2008,31: A38 Poster 0116 at the US Associated Professional Sleep Societies meeting, Baltimore, Jun. 2008.
Jenck F., Brisbare-Roch C, Aissaoui H, Koberstein R, Promotion of sleep through an orally available hypocretin/orexin antagonist in rats, dogs and humans, Eur Neuropsychopharm 2008,18 (Suppl4): S158, Lecture at the European College of Neuropsychopharmacology (ECNP) meeting, Barcelona, Sep. 2008.
Furlong TM, Daniel M. L.Vianna, LU Liu and Pascal Carrive, Extramural: Hypocretin/orexin contributes to the expression of some but not all forms of stress and arousal European Journal of Neuroscience, 2009, AOP: Oct 7, 2009.
Hoch M, Hoever P, Haschke M, Krähenbühl S, Alessi F, Dingemanse J, Biocomparison of two formulations of almorexant, a dual orexin receptor antagonist, including investigation of food effect, Poster at American College of Clinical Pharmacology, 38th Annual Meeting, San Antonio, Texas, Sep. 13-15, 2009.
Jae-Eunkang, Miranda M. Lim, Randall J. Bateman, James J. Lee, Liam P.Smyth, John R. Cirrito, Nobuhirofujiki, Seiji Nishino, David M. Holtzman, Extramural: Amyloid-βDynamics Are Regulated by Orexin and the Sleep-Wake Cycle, ScienceExpress, Sep. 24, 2009.

SUBSTITUTED 1,2,3,4-TETRAHYDROISOQUINOLINE DERIVATIVES

This application is a 371 of PCT/EP05/01879 filed Feb. 23, 2005.

The present invention relates to novel substituted 1,2,3,4-tetrahydroisoquinoline derivatives of the general formula (I) and their use as pharmaceuticals. The invention also concerns related aspects including processes for the preparation of the compounds, pharmaceutical compositions containing one or more compounds of the general formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies such as depression; anxiety; addictions, obsessive compulsive disorder; affective neurosis; depressive neurosis; anxiety neurosis; dysthymic disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders; sleep disorders; cardiovascular diseases, diabetes; appetite/taste disorders; vomiting/nausea; asthma; Parkinson's disease; Cushing's syndrome/disease; basophil adenoma; prolactinoma; hyperprolactinemia; hypopituitarism; hypophysis tumour/adenoma; hypothalamic diseases; inflammatory bowel disease; gastric dyskinesia; gastric ulcers; Froehlich's syndrome; hypophysis diseases, hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardial infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep apnea; narcolepsy; insomnia; parasomnia; and neurodegenerative disorders including nosological entities such as disinhibition-dementia-parkinsonism-amyotrophy complex; pallido-ponto-nigral degeneration epilepsy; seizure disorders and other diseases related to general orexin system dysfunction.

The present invention provides substituted 1,2,3,4-tetrahydroisoquinoline derivatives, which are non-peptide antagonists of human orexin receptors. These compounds are in particular of potential use in the treatment of e.g. eating disorders or sleep disorders.

Up to now, some low molecular weight compounds are known having a potential to antagonise either specifically $OX_1$ or $OX_2$, or both receptors at the same time. In some patent applications, e.g. SmithKline Beecham reported phenylurea, phenylthiourea and cinnamide derivatives as $OX_1$ selective antagonists (WO99/09024, WO00/47576 and WO00/47580). More recently, in their patent applications, SmithKline Beecham suggests 2-amino-methylpiperidine derivatives (WO01/96302), 3-aminomethyl-morpholine derivatives (WO02/44172) and N-aroyl cyclic amines (WO02/090355, WO03/002559 and WO03/002561) as orexin receptor antagonists. In WO01/85693, Banyu Pharmaceuticals claimed N-acyltetrahydroisoquinoline derivatives. Other orexin receptor antagonists such as novel benzazepine derivatives are disclosed in WO02/051838.

Actelion Pharmaceuticals Ltd. claimed 1,2,3,4-tetrahydroisoquinoline derivatives and their use as active ingredients in the preparation of pharmaceutical composition (WO01/68609). Furthermore, the use of solution-phase chemistry for the lead optimization of 1,2,3,4-tetrahydroisoquinoline derivatives as potential orexin receptor antagonists has been reported (Chimia, 2003, 57, 1-6).

It is well known that the adequate regulation of plasma concentrations of a drug during the treatment period is one of the crucial aspects in therapy. One very important mechanism for this regulation is the oxidation of a drug substance by cytochrome P450 (CYP) enzymes. The drug oxidation by CYP enzymes should be appropriate with respect to the desired therapeutic indication and a high inhibition of CYP enzymes should be avoided. This is due to the problem of drug-drug interaction, i.e. the increased plasma concentration of a drug by inhibition of a CYP enzyme from another drug.

The predominant drug-metabolising CYP 450s are CYP1A2, CYP2C9, CYP2C19, CYP2D6, CYP2E1 and CYP3A4 which represents about 30% of the total CYP enzymes. Many drugs are transformed by CYP3A4 and some drugs have no other metabolism pathway than this specific cytochrome. As a result, a low CYP3A4 inhibition is absolutely crucial for a chemical entity to become a drug candidate.

It has now been found that the compounds of the present invention have low affinities against CYP3A4. Further, it has also been observed that these compounds were active after oral administration. Compounds of the present invention are therefore useful for the treatment of diseases such as, for example, eating disorders or sleep disorders.

The following paragraphs provide definitions of the various chemical moieties for the compounds according to the invention and are intended to apply uniformly throughout the specification and claims unless an otherwise expressly set out definition provides a broader definition.

The term "alkyl", alone or in combination with other groups, means a straight-chain or branched-chain alkyl group with 1 to 6 carbon atoms, preferably a straight or branched-chain alkyl group with 1 to 4 carbon atoms. Examples of straight-chain and branched $C_1$-$C_6$ alkyl groups are methyl, ethyl, propyl, isopropyl, butyl, sec-butyl, isobutyl, tert-butyl, pentyl, hexyl, the isomeric pentyls, the isomeric hexyls, preferably methyl, ethyl, propyl, isopropyl, butyl, sec-butyl, isobutyl or tert-butyl.

The term "alkoxy", alone or in combination with other groups, means a R—O— group wherein R is an alkyl group as above-defined, such as methoxy, ethoxy, n-propoxy, iso-propoxy, n-butoxy, isobutoxy, sec-butoxy and tert-butoxy, preferably methoxy and ethoxy.

The expression "pharmaceutically acceptable salts" encompasses either salts with inorganic acids or organic acids like hydrochloric acid, hydrobromic acid, hydroiodic acid, sulfuric acid, phosphoric acid, nitric acid, citric acid, formic acid, acetic acid, maleic acid, tartaric acid, fumaric acid, benzoic acid, pamoic acid, stearic acid, methanesulfonic acid, p-toluenesulfonic acid, salicylic acid, succinic acid, trifluoroacetic acid, and the like that are non toxic to living organisms or in case the compound of formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or poly-acid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

A first aspect of the invention consists of novel substituted 1,2,3,4-tetrahydroisoquinoline derivatives of the following general formula (I):

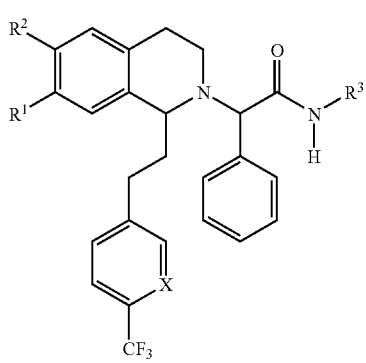

wherein $R^1$ and $R^2$ independently represent hydrogen or $C_1$-$C_4$ alkoxy;

$R^3$ represents $C_1$-$C_6$-alkyl;

X represents —CH— or a nitrogen atom.

Also encompassed by the present invention are compounds of formula I and optically pure enantiomers, mixtures of enantiomers, racemates, optically pure diastereoisomers, mixtures of diastereoisomers, diastereoisomeric racemates, mixture of diastereoisomeric racemates, meso forms and pharmaceutically acceptable salts, solvent complexes and morphological forms, thereof.

Any reference to a compound of General Formula (I) is to be understood as referring also to configurational isomers, mixtures of enantiomers such as racemates, diastereomers, mixtures of diastereomers, diastereomeric racemates, and mixtures of diastereomeric racemates, as well as salts, especially pharmaceutically acceptable salts, solvent complexes, and morphological forms, as appropriate and expedient.

As above-mentioned, the present invention encompasses also solvation complexes of compounds of general Formula (I). The solvation can be effected in the course of the manufacturing process or can take place separately, e.g. as a consequence of hygroscopic properties of an initially anhydrous compound of general Formula (I). The invention further encompasses different morphological forms, e.g crystalline forms, of compounds of general Formula (I) and their salts and solvation complexes. Particular heteromorphs may exhibit different dissolution properties, stability profiles, and the like, and are all included in the scope of the present invention.

Preferred substituted 1,2,3,4-tetrahydroisoquinoline derivatives are those wherein $R^1$ and $R^2$ both represent a $C_1$-$C_4$ alkoxy group, particularly a methoxy group.

In a preferred embodiment according to the invention, X represents —CH—. In another preferred embodiment, X represents a nitrogen atom.

In another preferred embodiment according to the invention, $R^3$ represents a methyl group.

In a particularly preferred embodiment according to the invention, $R^1$ and $R^2$ represent a methoxy group, X represents —CH— and $R^3$ represents $C_1$-$C_6$-alkyl.

Examples of preferred compounds are selected from the group consisting of:

2-{6,7-Dimethoxy-1-[2-(4-trifluoromethyl-phenyl)-ethyl]-3,4-dihydro-1H-isoquinolin-2-yl}-N-methyl-2-phenyl-acetamide;

2-{6,7-Dimethoxy-1-[2-(6-trifluoromethyl-pyridin-3-yl)-ethyl]-3,4-dihydro-1H-iso-quinolin-2-yl}-N-methyl-2-phenyl-acetamide.

The compounds pursuant to general formula (I) are useful in the preparation of a medicament for the prevention or treatment of diseases selected from the group consisting of depression; anxiety; addictions; obsessive compulsive disorder; affective neurosis; depressive neurosis; anxiety neurosis; dysthymic disorder; mood disorder; sexual dysfunction; psychosexual dysfunction; schizophrenia; manic depression; delirium; dementia; severe mental retardation and dyskinesias such as Huntington's disease and Tourette syndrome; diabetes; appetite/taste disorders; vomiting/nausea; asthma; Parkinson's disease; Cushing's syndrome/disease; basophil adenoma; prolactinoma; hyperprolactinemia; hypopituitarism; hypophysis tumour/adenoma; hypothalamic diseases; inflammatory bowel disease; gastric dyskinesia; gastric ulcers; Froehlich's syndrome; hypophysis diseases, hypothalamic hypogonadism; Kallman's syndrome (anosmia, hyposmia); functional or psychogenic amenorrhea; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardial infarction; ischemic or haemorrhagic stroke; subarachnoid haemorrhage; ulcers; allergies; benign prostatic hypertrophy; chronic renal failure; renal disease; impaired glucose tolerance; migraine; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. by HIV; post-chemotherapy pain; post-stroke pain; post-operative pain; neuralgia; conditions associated with visceral pain such as irritable bowel syndrome; migraine and angina; urinary bladder incontinence e.g. urge incontinence; tolerance to narcotics or withdrawal from narcotics; sleep disorders; eating disorders; cardiovascular disorders; neurodegenerative disorders; sleep apnea; narcolepsy; insomnia; parasomnia; and neurodegenerative disorders including nosological entities such as disinhibition-dementia-parkinsonism-amyotrophy complex; pallido-ponto-nigral degeneration epilepsy; seizure disorders and other diseases related to general orexin system dysfunctions.

Compounds of the general formula (I) are particularly suitable for use in the treatment of diseases or disorders selected from the group consisting of eating disorders or sleep disorders.

Eating disorders may be defined as comprising metabolic dysfunction; dysregulated appetite control; compulsive obesities; emeto-bulimia or anorexia nervosa. This pathologically modified food intake may result from disturbed appetite (attraction or aversion for food); altered energy balance (intake vs expenditure); disturbed perception of food quality (high fat or carbohydrates, high palatability); disturbed food availability (unrestricted diet or deprivation) or disrupted water balance.

Sleep disorders include insomnias, narcolepsy and other disorders of excessive sleepiness, sleep-related dystonias; restless leg syndrome; sleep apneas; jet-lag syndrome; shift-work syndrome, delayed or advanced sleep phase syndrome. Insomnias are defined as comprising sleep disorders associated with aging; intermittent treatment of chronic insomnia; situational transient insomnia (new environment, noise) or short-term insomnia due to stress; grief; pain or illness.

A further object of the invention is a pharmaceutical composition containing at least one compound according to general formula (I) and a pharmaceutically acceptable carrier material.

Another object of the present invention is a method for the treatment or prophylaxis of diseases, which are related to the orexin receptors such as eating disorders or sleep disorders comprising the administration to a patient of a therapeutically effective amount of a 1,2,3,4-tetrahydroisoquinoline derivative according to general formula (I).

In a preferred embodiment of the invention, this amount is comprised between 1 mg and 1000 mg per day, particularly from 2 mg to 500 mg per day, more particularly from 5 mg to 200 mg per day.

The present invention also concerns a process for the preparation of a pharmaceutical composition comprising a 1,2,3,4-tetrahydroisoquinoline derivative according to general formula (I) by mixing one or more active ingredients according to general formula (I) with a carrier material in a manner known per se.

The compounds of general formula (I) and their pharmaceutically acceptable salts can be used as medicament (e.g. in the form of pharmaceutical preparations). The pharmaceutical preparations can be administered enterally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions), or topically, e.g. in the form of ointments, cream or oils.

The compounds of general formula (I) and their pharmaceutically acceptable salts can be processed with pharmaceutically inert, inorganic or organic adjuvants for the production of tablets, coated tablets, dragées, and hard gelatine capsules. Lactose, cornstarch or derivatives thereof, talc, stearic acid or its salts etc. can be used, for example, as such adjuvants for tablets, dragées, and hard gelatine capsules. Suitable adjuvants for soft gelatine capsules, are for example, vegetable oils, waxes, fats, semi-solid substances and liquid polyols, etc.

Suitable adjuvants for the production of solutions and syrups are, for example, water, alcohol, polyols, saccharose, invert sugar, glucose etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc.

The above-described components for orally administered or injectable compositions are merely representative examples. Further materials as well as processing techniques and the like are set out in *Remington's Pharmaceutical Sciences,* 20$^{th}$ Edition, 2001, Marck Publishing Company, Easton, Pa., which is incorporated herein by reference.

The compounds of this invention can also be administered in sustained release forms by using known sustained release drug delivery systems.

A further object of the invention is a process for the preparation of 1,2,3,4-tetrahydroisoquinoline derivatives according to general formula (I). Compounds according to general formula (I) of the present invention are prepared according to the general sequence of reactions outlined in the schemes below wherein X, $R^1$, $R^2$ and $R^3$ are as defined in general formula (I). The compounds obtained may also be converted into pharmaceutically acceptable salts thereof in a manner known per se.

As described in Scheme 1 below, the key-intermediates in the synthesis of compounds of the general formula (I) are 1-substituted 3,4-dihydroisoquinoline derivatives. These compounds are prepared either by cyclisation of N-phenethyl-propionamides with POCl$_3$ or by alkylation of 1-methyl-3,4-dihydroisoquinolines with alkyl bromides. The 3,4-dihydroisoquinolines obtained are reduced to 1,2,3,4-tetrahydroisoquinolines with sodium borohydride to give the products as racemic mixtures. Enantiomerically highly enriched 1,2,3,4-tetrahydroisoquinolines are obtained by a transfer hydrogenation of the respective 3,4 dihydroisoquinoline in the presence of a chiral Ru(II)-complex (chiral catalyst), which was originally described by R. Noyori et al. (*J. Am. Chem. Soc.* 1996, 118, 4916-4917 and WO 97/20789). The chiral catalyst (Ru(II) complex) used is as follows:

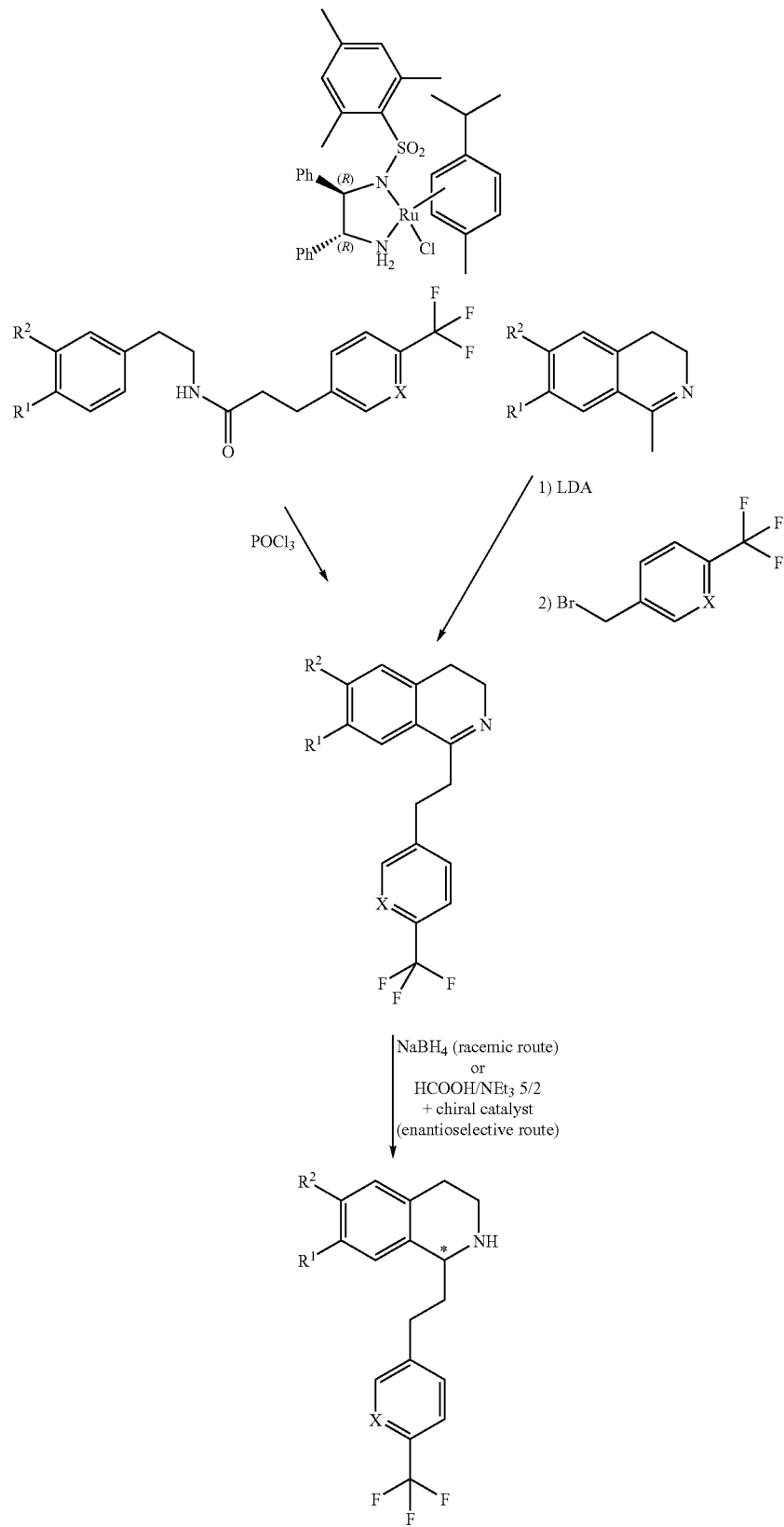

As illustrated in Scheme 2 and Scheme 3 below, 1,2,3,4-tetrahydroisoquinoline intermediates according to the invention can be converted to compounds of general formula (I) following one of the three different synthetic routes a) b) or c). In route a), the 1,2,3,4-tetrahydroisoquinoline is alkylated with a substituted 2-bromo-acetic acid methyl ester. The obtained ester is hydrolyzed to the corresponding acid and finally converted to the amide by an amide-coupling reaction with the desired amine in the presence of a coupling reagent. In route b), the side-chain is introduced by a direct alkylation of the respective 1,2,3,4-tetrahydroisoquinoline with a 2-bromo-acetamide derivative:

1,2,3,4-tetrahydroisoquinoline derivatives of general formula (I) can also be prepared in a stereoselective manner starting from enantiomerically pure methyl (S)-(+)-mandelate following route c) (cf. Scheme 3 hereinafter). By treating the ester with an alcoholic amine solution the corresponding amide is obtained which can be tosylated with p-toluenesulphonyl chloride. In a last step the tosylate is coupled with a 1,2,3,4-tetrahydroisoquinoline derivative to give the respective compound of general formula (I).

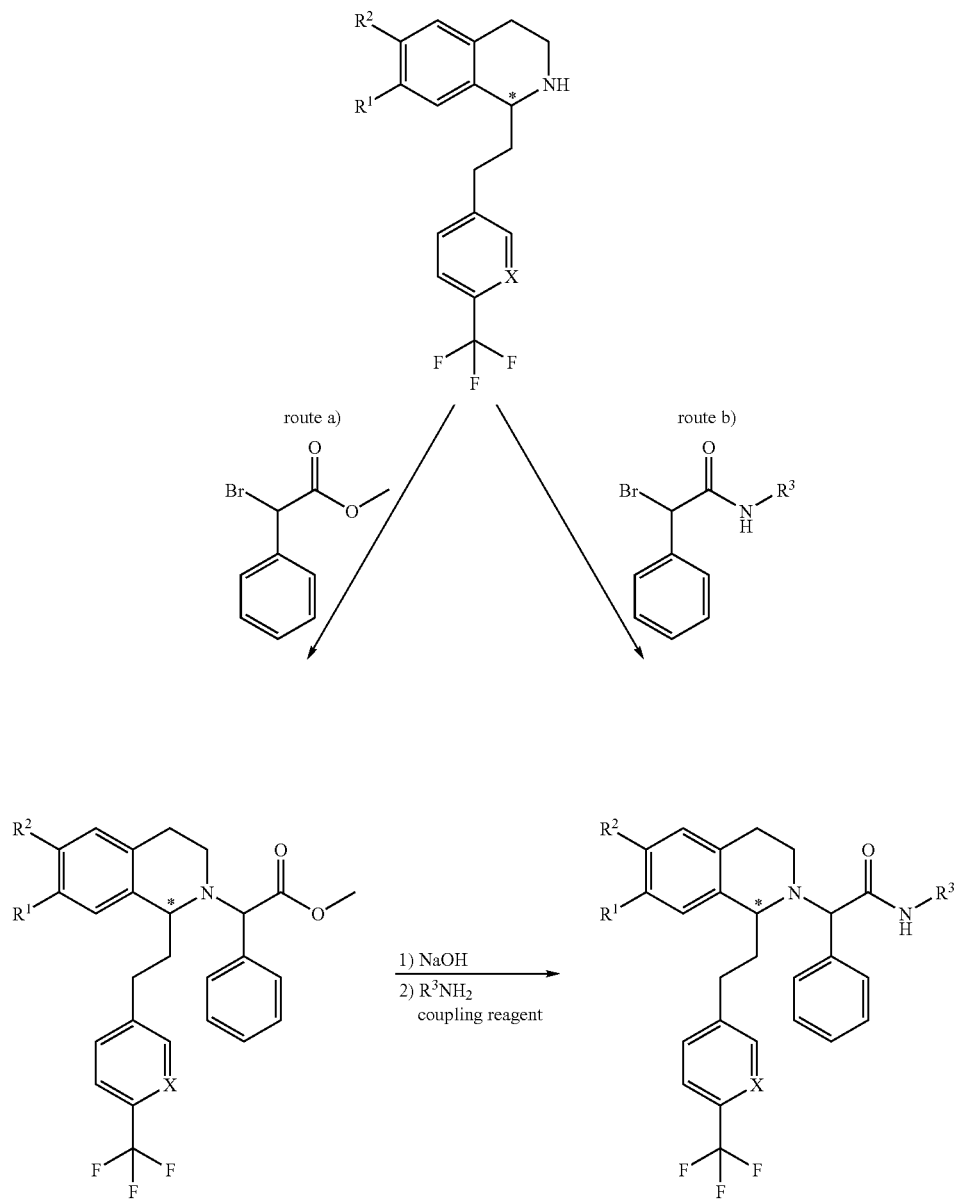

Scheme 3

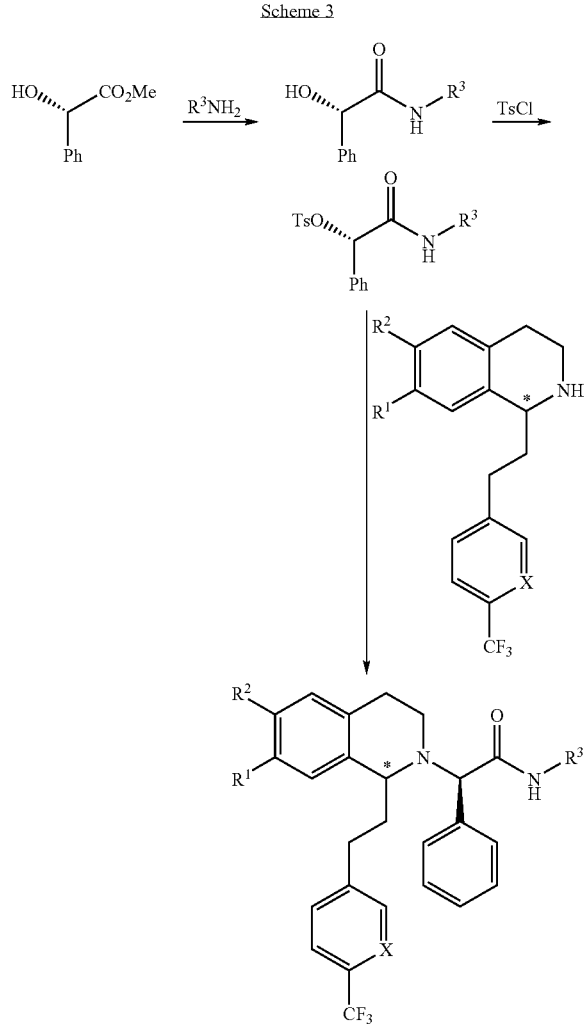

The 1,2,3,4-tetrahydroisoquinoline derivatives exemplified in this invention may be prepared from readily available starting materials using the following general methods and procedures. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art using routine optimisation procedures.

Experimental Section:

Abbreviations:

| | |
|---|---|
| aq. | aqueous |
| atm | atmosphere |
| BSA | Bovine Serum Albumine |
| CHO | Chinese Hamster Ovary |
| d | Day(s) |
| DCM | Dichloromethane |
| DIPEA | Diisopropylethylamine |
| DMAP | N,N-dimethyl-4-aminopyridine |
| DMF | Dimethylformamide |
| DMSO | Dimethylsulfoxide |
| EA | Ethyl acetate |
| EDC | 1-(3-Dimethylaminopropyl)-3-ethylcarbodiimide |
| ES | Electron Spray |
| FCS | Fetal Calf Serum |
| FLIPR | Fluorescent Imaging Plate Reader |
| h | hour |
| HBSS | Hank's Balanced Salt Solution |
| HEPES | 4-(2-Hydroxyethyl)-piperazine-1-ethanesulfonic acid |
| HOBt | Hydroxybenzotriazol |
| HPLC | High Performance Liquid Chromatography |
| Hex | Hexane |
| HV | High Vacuum conditions |
| LC | Liquid Chromatography |
| LDA | Lithium diisopropylamide |
| MeOH | Methanol |
| min | minutes |
| MS | Mass Spectroscopy |
| p.o. | per os |
| prep. | preparative |
| PyBOP | Benzotriazole-1-yl-oxy-tris-pyrrolidino-phosphonium-hexafluorophosphate |
| $R_f$ | Retention front |
| RT | Room temperature |
| rt | retention time |
| sat. | saturated |
| tlc | thin layer chromatography |
| THF | Tetrahydrofuran |

Chemistry

The following examples illustrate the preparation of pharmacologically active compounds of the invention but do not at all limit the scope thereof.

All temperatures are stated in ° C.

All analytical and preparative HPLC investigations on non-chiral phases are performed using RP-C18 based columns. Analytical HPLC investigations are performed on two different instruments with cycle-times of ~2.5 min and ~3.5 min respectively. For HPLC separations on chiral phases a Chiralcel OD column from Daicel Chemical Industries is used. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; q=quartet, m=multiplet, b=broad, coupling constants are given in Hz); by LC-MS, rt is given in min; by TLC (TLC-plates from Merck, Silica gel 60 $F_{254}$); or by melting point.

A. Synthesis of Propionic Acid Derivatives

1. Synthesis of 3-(6-trifluoromethyl-pyridin-3-yl)-propionic acid 1.1 Synthesis of 3-(6-trifluoromethyl-pyridin-3-yl)-acrylic acid methyl ester

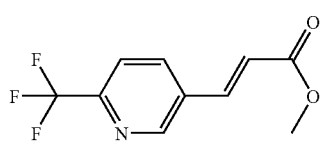

A solution of 6-trifluoromethyl-pyridine-3-carbaldehyde (570 mg) in DCM (1.0 mL) is added to a solution of (triphenyl-$\lambda^5$-phosphanylidene)-acetic acid methyl ester (990 mg) in DCM (2.5 ml). The mixture is stirred under nitrogen at reflux for 20 h and concentrated in vacuo. The residue is purified by flash chromatography (EA/heptane 3/7) to give the desired unsaturated ester as a white solid.

¹H-NMR (300 MHz, CDCl₃): δ=3.85 (s, 3H), 6.59 (d, J=16.2 Hz, 1H), 7.70 (d, J=16.2 Hz, 1H), 7.71 (d, J=8.1 Hz, 1H), 7.98 (dd, J=8.1 Hz, J=2.1 Hz, 1H), 8.84 (bs, 1H).

1.2 Synthesis of 3-(6-trifluoromethyl-pyridin-3-yl)-propionic acid methyl ester

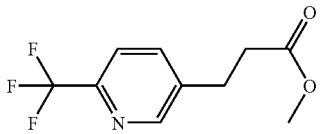

A solution of 3-(6-trifluoromethyl-pyridin-3-yl)-acrylic acid methyl ester (720 mg) in methanol (5.0 mL) is treated with Pd/C (10%, 240 mg) and stirred under a hydrogen atmosphere (~1 bar) at RT for 20 h. The suspension is filtered through Celite and concentrated in vacuo to give the propionic acid ester as a colorless oil.

¹H-NMR (300 MHz, CDCl₃): δ=2.69 (t, J=7.4 Hz, 2H), 3.05 (t, J=7.4 Hz, 2H), 3.68 (s, 3H), 7.60 (d, J=7.8 Hz, 1H), 7.71 (bd, J=8.1 Hz, 1H), 8.58 (bs, 1H).

1.3. Synthesis of 3-(6-trifluoromethyl-pyridin-3-yl)-propionic acid

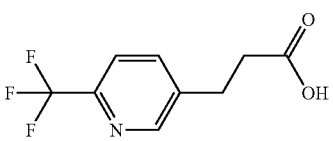

Lithium hydroxide monohydrate (330 mg) is added in one portion to a solution of 3-(6-trifluoromethyl-pyridin-3-yl)-propionic acid methyl ester (610 mg) in a mixture of THF (15 mL) and water (5 mL). The mixture is stirred for 20 h at RT. DCM and aqueous HCl (1.0 M) are added, the layers are separated and the aqueous layer is extracted twice with DCM. The combined organic extracts are dried over MgSO₄ and concentrated in vacuo to give the desired propionic acid as a beige solid.

¹H-NMR (300 MHz, CDCl₃): δ=2.75 (t, J=7.4 Hz, 2H), 3.06 (t, J=7.4 Hz, 2H), 7.62 (d, J=8.1 Hz, 1H), 7.73 (bd, J=8.1 Hz, 1H), 8.62 (bs, 1H).

B. Synthesis of 2-Bromo-Acetamide Derivatives

1. Synthesis of 2-bromo-N-methyl-2-phenyl-acetamide

1.1. Synthesis of N-hydroxy-N-methyl-2-phenyl-acetamide

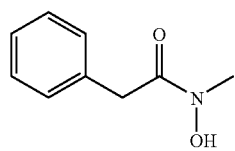

At 0° C. phenyl-acetyl chloride (11.2 mL) is added drop wise to a solution of N-methyl-hydroxylamine hydrochloride (7.07 g) and triethylamine (59 mL) in DCM (300 mL). After stirring for 90 min a sat. aqueous NaHCO₃ solution is added, the layers are separated and the aqueous layer is extracted twice with DCM (2×200 mL). The solvents are removed in vacuo and the residue is purified by flash chromatography (EA/heptane 1/1) to give the desired N-hydroxy-acetamide as a colorless liquid.

LC-MS: rt=0.63 min, 166 (M+1, ES+).

1.2. Synthesis of 2-bromo-N-methyl-2-phenyl-acetamide

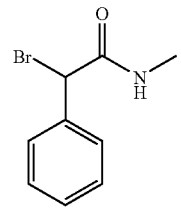

At 0° C. triethylamine (5.49 mL) is added to a solution of N-hydroxy-N-methyl-2-phenyl-acetamide (6.5 g) in DCM (200 mL). The mixture is treated drop wise with a solution of methanesulfonyl chloride (3.21 mL) in DCM (60 mL). After 2 h water (150 mL) is added, the layers are separated and the aqueous layer is extracted twice with EA (2×100 mL). The organic extracts are combined and concentrated in vacuo to give the crude mesylate as a pale yellow oil.

The mesylate is dissolved in acetonitrile (200 mL). Lithium bromide (15.3 g) is added and the reaction mixture is treated with ultrasound for 5 min. After addition of diisopropyl-ethylamine (6.78 mL) the mixture is again treated with ultrasound for 5 min and stirred for additional 60 min at room temperature. Water (150 mL) and ethyl acetate (200 mL) are added, the layers are separated and the aqueous layer is extracted twice with ethyl acetate (2×200 mL). The combined organic extracts are concentrated in vacuo and purified by flash chromatography (ethyl acetate/heptane 2:3) to give the desired bromide as a white solid.

LC-MS: rt=0.75 min, 228 (M+1, ES+).

C. Synthesis of Toluene-4-Sulfonic Acid (S)-Methylcarbamoyl-Phenyl-Methyl Ester

1. Synthesis of (S)-2-hydroxy-N-methyl-2-phenyl-acetamide

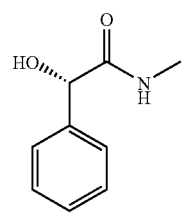

Methyl (S)-(+)-mandelate (17 g) is dissolved in a solution of methylamine in methanol (230 mL, 2.0 M) and kept at RT for 1 d. Another portion of methylamine in methanol (10 mL, 2.0 M) is added. A third portion of methylamine in methanol (10 mL, 2.0 M) is added one day later. After additional 24 h the solvents are removed in vacuo to give the desired mandelamide as pale yellow crystals, which are used without further purification.

LC-MS: rt=0.52 min, 166 (M+1, ES+).

2. Synthesis of toluene-4-sulfonic acid (S)-methylcarbamoyl-phenyl-methyl ester

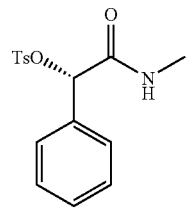

At RT DIPEA (2.74 mL) and DMAP (145 mg) are added to a solution of (S)-2-hydroxy-N-methyl-2-phenyl-acetamide (2.4 g) in DCM (50 mL). The mixture is treated portionwise with p-toluenesulfonyl chloride (2.75 g) and kept for 2 h at RT. The solvent is removed in vacuo and the residue is dissolved in ethyl acetate. The solution is washed twice with sat. NaHCO$_3$ solution and once with brine, the solvents are removed in vacuo and the residue is recrystallized from ethyl acetate/tert.-butylmethylether to give the tosylate as white crystals.

LC-MS: rt=0.93 min, 320 (M+1, ES+).

D. Synthesis of N-((1R,2R)-2-amino-1,2-diphenyl-ethyl)-2,4,6-trimenthyl-benzene-sulfonamide (Catalyst Precursor)

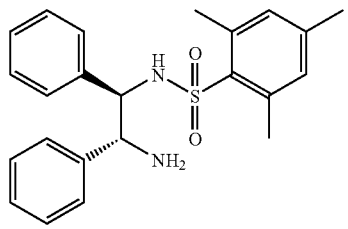

At 0° C. a solution of mesitylenesulfonyl chloride (3.09 g) in THF (150 ml) is added drop wise to a suspension of (1R, 2R)-1,2-diphenyl-ethane-1,2-diamine (3.00 g), diisopropylethylamine (3.87 mL) and potassium carbonate (3.12 g) in a mixture of THF (120 mL) and DMF (30 mL). After 3 h water (300 mL) and ethyl acetate (300 mL) are added, the layers are separated and the aqueous layer is extracted three times with ethyl acetate (3×300 mL). The solvents are removed in vacuo and the residue is purified by preparative HPLC chromatography. To remove the formic acid the obtained product is extracted with sat. NaHCO$_3$ solution/ethyl acetate to give the mono-sulfonamide as a white solid.

LC-MS: rt=0.82 min, 395 (M+1, ES+).

E. Synthesis of Phenylethylamides (General Procedure)

A solution of the respective phenylethylamine (110 mmol) in toluene (350 mL) is treated with the respective propionic acid derivative (110 mmol), refluxed for 90 h in the presence of a Dean-Stark trap and cooled slowly to RT. The precipitate is filtered off and dried under vacuum to give the desired amide.

1. Synthesis of N-[2-(3,4-dimethoxy-phenyl)-ethyl]-3-(4-trifluoromethyl-phenyl)-propionamide

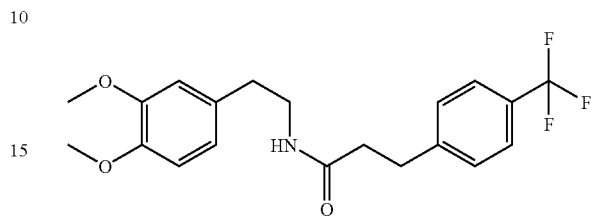

This compound is prepared by reaction of 3,4-dimethoxyphenylethylamine and 4-(trifluoromethyl)-hydrocinnamic acid.

LC-MS: rt=0.97 min, 382 (M+1, ES+).

2. Synthesis of N-[2-(3,4-dimethoxy-phenyl)-ethyl]-3-(6-trifluoromethyl-pyridin-3-yl)-propionamide

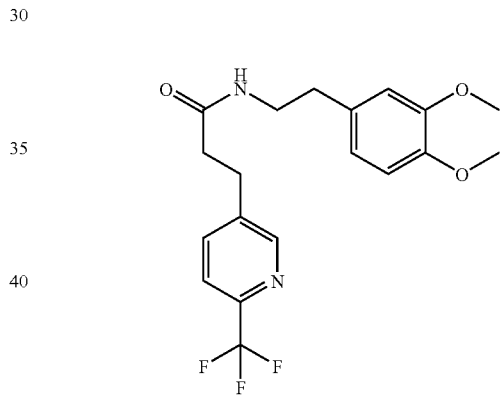

This compound is prepared by reaction of 3,4-dimethoxyphenylethylamine and 3-(6-trifluoromethyl-pyridin-3-yl)-propionic acid.

LC-MS: rt=0.88 min, 383 (M+1, ES+).

F. Synthesis of 3,4-Dihydroisoquinoline Derivatives Via Amide-Cyclisation (General Procedure)

Phosphorus oxychloride (123 mmol) is added to a suspension of the respective amide (55.3 mmol) in acetonitrile (300 mL). The mixture is refluxed for 90 min and the solvents are removed in vacuo. Methanol (100 mL) is added and evaporated again. The obtained product is recrystallized from dioxane or dioxane/ethanol. After filtration the obtained hydrochloride salt is converted to the free base by addition of saturated aqueous NaHCO$_3$ solution and extraction with dichloromethane. The solvents are removed in vacuo to give the respective dihydroisoquinoline.

1. Synthesis of 6,7-dimethoxy-1-[2-(4-trifluoromethyl-phenyl)-ethyl]-3,4-dihydroisoquinoline

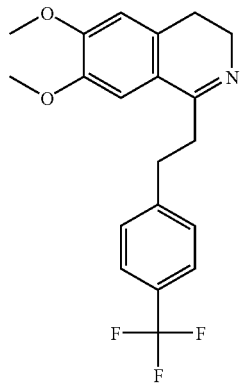

This compound is prepared by cyclisation of N-[2-(3,4-dimethoxy-phenyl)-ethyl]-3-(4-trifluoromethyl-phenyl)-propionamide.

LC-MS: rt=0.81 min, 364 (M+1, ES+).

2. Synthesis of 6,7-dimethoxy-1-[2-(6-trifluoromethyl-pyridin-3-yl)-ethyl]-3,4-dihydroisoquinoline

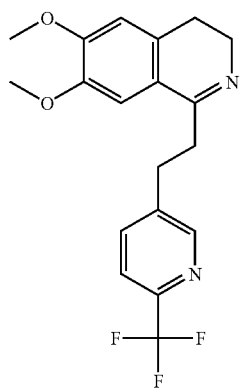

This compound is prepared by cyclisation of N-[2-(3,4-dimethoxy-phenyl)-ethyl]-3-(6-trifluoromethyl-pyridin-3-yl)-propionamide.

LC-MS: rt=0.73 min, 365 (M+1, ES+)

G. Synthesis of 1,2,3,4-tetrahydroisoquinolines

1. Synthesis of 1,2,3,4-tetrahydroisoquinolines via Bischler-Napieralski-reaction (General Procedure)

To a suspension of the respective amide (44.8 mmol) in acetonitrile (500 mL) is added phosphorus oxychloride (224 mmol). The mixture is heated to reflux for 2 h and the solvent is removed in vacuo. The resulting oil is taken up in either toluene or MeOH (20 mL), evaporated to dryness, dissolved in MeOH (200 mL) and cooled to 0° C. NaBH$_4$ (135 mmol) is added in small portions and the reaction mixture is stirred for 2 h. The solvent is removed in vacuo, EA (400 mL) and water (400 mL) are added, the layers are separated and the aqueous layer is extracted three times with EA (3×200 mL). The combined organic extracts are concentrated in vacuo to give the following 1,2,3,4-tetra-hydroisoquinolines as racemic mixtures, which are purified by crystallization of the hydrochloride salt from isopropanol.

1.1. Synthesis of rac-6,7-dimethoxy-1-[2-(4-trifluoromethyl-phenyl)-ethyl]-1,2,3,4-tetrahydroisoquinoline

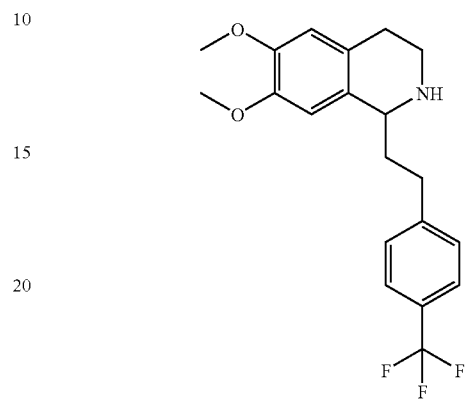

This compound is prepared by reaction of N-[2-(3,4-dimethoxy-phenyl)-ethyl]-3-(4-trifluoromethyl-phenyl)-propionamide.

LC-MS: rt=0.85 min, 366 (M+1, ES+).

1.2. Synthesis of 6,7-dimethoxy-1-[2-(6-trifluoromethyl-pyridin-3-yl)-ethyl]-1,2,3,4-tetrahydroisoquinoline

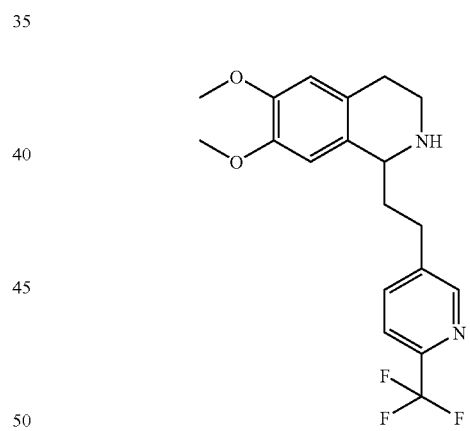

This compound is prepared by reaction of N-[2-(3,4-dimethoxy-phenyl)-ethyl]-3-(6-trifluoromethyl-pyridin-3-yl)-propionamide.

LC-MS: rt=0.73 min, 367 (M+1, ES+).

2. Synthesis of 1,2,3,4-Tetrahydroisoquinolines Via Transfer Hydrogenation (General Procedure)

Dichloro-(p-cymene)ruthenium (II) dimer (0.20 mmol) is added to a solution of N-((1R,2R)-2-amino-1,2-diphenyl-ethyl)-2,4,6-trimethylbenzene-sulfonamide (0.40 mmol) and triethylamine (0.80 mmol) in acetonitrile (3.0 mL). The mixture is stirred for 1 h at 80° C. and added to a solution of the respective dihydroisoquinoline (28.0 mmol) in dichloromethane (30 mL). An azeotropic mixture of formic acid and triethylamine (5:2, 14 mL) is added (gas evolution). After 90 min a sat. aqueous NaHCO₃ solution (200 mL) is added to the dark red solution. The layers are separated, the aqueous layer is extracted twice with DCM (2×200 mL) and the combined organic extracts are concentrated in vacuo. The residue is dissolved in isopropanol (1600 mL) and treated with a solution of HCl in isopropanol (5-6 M, 10 mL). The obtained hydrochloride salt is recrystallized to give the respective 1,2,3,4-tetrahydroisoquinoline with high enantiomeric excess as determined by chiral HPLC. The hydrochloride salt is converted to the free base by extraction with sat. NaHCO₃ solution/dichloromethane. The absolute configuration of the respective product is assigned in analogy to the literature (N. Uematsu, A. Fujii, S. Hashiguchi, T. Ikariya, R. Noyori, *J. Am. Chem. Soc.* 1996, 118, 4916-4917).

2.1 Synthesis of (1S)-6,7-dimethoxy-1-[2-(4-trifluoromethyl-phenyl)-ethyl]-1,2,3,4-tetrahydroisoquinoline

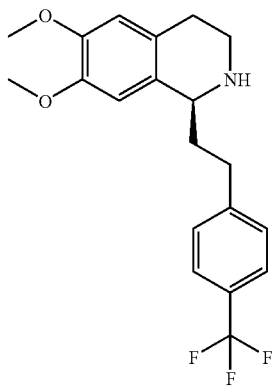

This compound is prepared by transfer hydrogenation of 6,7-dimethoxy-1-[2-(4-trifluoromethyl-phenyl)-ethyl]-3,4-dihydroisoquinoline.

LC-MS: rt=0.80 min, 366 (M+1, ES+).
chiral HPLC: rt=12.0 min (hexane/ethanol 9/1; enantiomer: rt=17.1 min).

2.2 Synthesis of (1S)-6,7-dimethoxy-1-[2-(6-trifluoromethyl-pyridin-3-yl)-ethyl]-1,2,3,4-tetrahydroisoquinoline

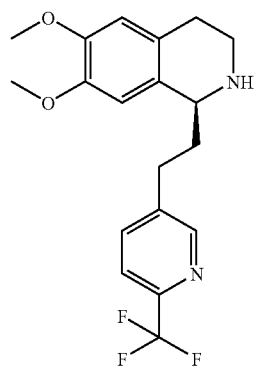

This compound is prepared by transfer hydrogenation of 6,7-dimethoxy-1-[2-(6-trifluoromethyl-pyridin-3-yl)-ethyl]-3,4-dihydroisoquinoline.

LC-MS: rt=0.73 min, 367 (M+1, ES+).
chiral HPLC: rt=10.9 min (hexane/ethanol 4/1; enantiomer: rt=24.4 min).

3. Synthesis of 1,2,3,4-Tetrahydroisoquinolines Via Alkylation of 1-Methyl-3,4-Dihydroisoquinolines (General Procedure)

At 0° C. a solution of n-BuLi in hexane (1.6M, 0.63 mmol) is added drop wise to a mixture of 6,7-dimethoxy-1-methyl-3,4-dihydroisoquinoline (0.50 mmol) and diisopropylamine (0.63 mmol) in THF (1.0 mL). The reaction mixture is stirred at RT for 1 h and added at 0° C. to a solution of the respective benzyl bromide (0.50 mmol) in THF (1.0 mL). The solution is stirred for 1 h, warmed up to RT and diluted with DCM (3.0 mL).

In a second flask dichloro(p-cymene)ruthenium (II) dimer (0.15 mmol) is added to a solution of N-((1R,2R)-2-amino-1,2-diphenyl-ethyl)-2,4,6-trimethyl-benzene-sulfonamide (0.30 mmol) and triethylamine (0.60 mmol) in acetonitrile (3.3 mL). The mixture is stirred for 1 h at 80° C. A portion of this solution (0.10 mL) is added to the solution of the respective dihydroisoquinoline (described above). An azeotropic mixture of formic acid and triethylamine (5:2, 0.3 mL) is added (gas evolution). After 2 d the mixture is concentrated in vacuo and purified by prep. HPLC to give the respective 1,2,3,4-tetra-hydroisoquinoline.

The enantiomeric excess is determined by chiral HPLC.
The absolute configuration of the respective product is assigned in analogy to the literature (N. Uematsu, A. Fujii, S. Hashiguchi, T. Ikariya, R. Noyori, *J. Am. Chem. Soc.* 1996, 118, 4916-4917).

3.1. Synthesis of (1S)-6,7-dimethoxy-1-[2-(4-trifluoromethyl-phenyl)-ethyl]-1,2,3,4-tetrahydroisoquinoline

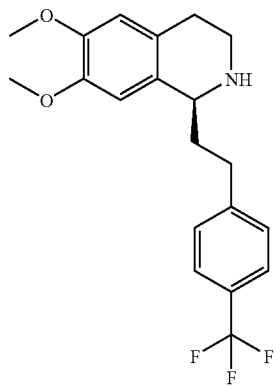

This compound is prepared by alkylation of 6,7-dimethoxy-1-methyl-3,4-dihydroisoquinoline with 1-bromomethyl-4-trifluoromethyl-benzene.

LC-MS: rt=0.80 min, 366 (M+1, ES+).
chiral HPLC: rt=12.0 min (hexane/ethanol 9/1; enantiomer: rt=17.1 min).

H. Synthesis of (3,4-Dihydro-1H-Isoquinolin-2-yl)-Phenyl-Acetic Acid Methyl Ester Derivatives (General Procedure)

DIPEA (43.0 mmol) and α-bromo-phenyl-acetic acid methyl ester (21.5 mmol) are added successively to a solution of the respective 1,2,3,4-tetrahydroisoquinoline (21.5 mmol)

in either THF, dioxane or toluene (150 mL). The mixture is refluxed for 20 h and allowed to reach RT. Water (250 mL) and EA (200 mL) are added, the layers were separated and the aqueous layer is extracted twice with EA (2×100 mL). The combined organic extracts are concentrated in vacuo and either purified by flash chromatography or used without further purification. The following ester derivatives described hereinafter are obtained.

1. Synthesis of {6,7-dimethoxy-1-[2-(4-trifluoromethyl-phenyl)-ethyl]-3,4-dihydro-1H-isoquinolin-2-yl}-phenyl-acetic acid methyl ester

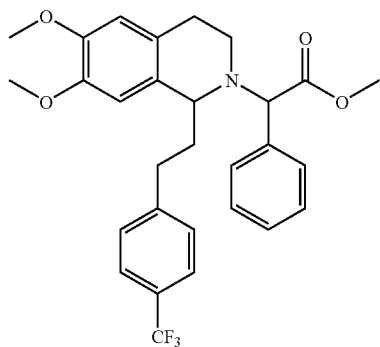

This compound is prepared by reaction of 6,7-dimethoxy-1-[2-(4-trifluoromethyl-phenyl)-ethyl]-1,2,3,4-tetrahydroisoquinoline with α-bromo-phenyl-acetic acid methyl ester.

LC-MS: rt=0.93 min, 514 (M+1, ES+).

2. Synthesis of {6,7-dimethoxy-1-[2-(6-trifluoromethyl-pyridin-3-yl)-ethyl]-3,4-dihydro-1H-isoquinolin-2-yl}-phenyl-acetic acid methyl ester

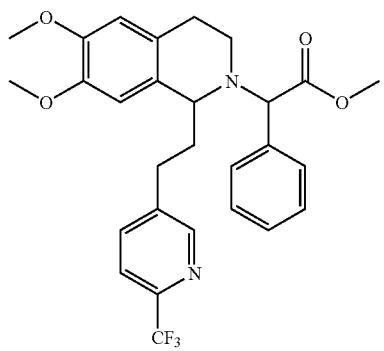

This compound is prepared by reaction of 6,7-dimethoxy-1-[2-(6-trifluoromethyl-pyridin-3-yl)-ethyl]-1,2,3,4-tetrahydroisoquinoline with α-bromo-phenyl-acetic acid methyl ester.

LC-MS: rt=1.68 min, 515 (M+1, ES+).

3. Synthesis of {(1S)-6,7-dimethoxy-1-[2-(4-trifluoromethyl-phenyl)-ethyl]-3,4-dihydro-1H-isoquinolin-2-yl}-phenyl-acetic acid methyl ester

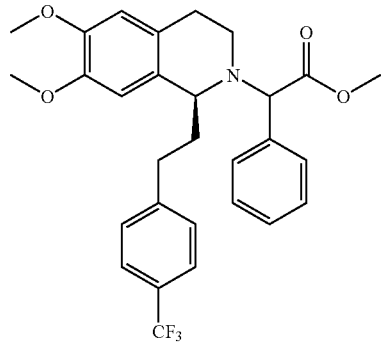

This compound is prepared by reaction of (1S)-6,7-dimethoxy-1-[2-(4-trifluoromethyl-phenyl)-ethyl]-1,2,3,4-tetrahydroisoquinoline with α-bromo-phenyl-acetic acid methyl ester.

LC-MS: rt=0.93 min, 514 (M+1, ES+).

I. Synthesis of (3,4-Dihydro-1H-Isoquinolin-2-yl)-Phenyl-Acetic Acid Derivatives (General Procedure)

A solution of sodium hydroxide in water (2.0M, 50 mL) is added to a solution of the respective ester (21.5 mmol) in methanol (400 mL). The mixture is heated to 60° C. and stirred for 20 h. Most of the methanol is removed in vacuo and the residue is taken up in sodium hydroxide solution (2.0M, 20 mL), water (100 mL) and DCM (100 mL). The layers are separated and the aqueous layer is extracted three times with DCM (3×100 mL). The combined organic extracts are concentrated in vacuo to give the respective carboxylic acid, which is used without further purification:

1. Synthesis of {6,7-dimethoxy-1-[2-(4-trifluoromethyl-phenyl)-ethyl]-3,4-dihydro-1H-isoquinolin-2-yl}-phenyl-acetic acid

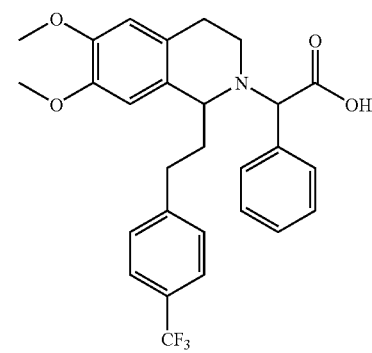

This compound is prepared by saponification of {6,7-dimethoxy-1-[2-(4-trifluoromethyl-phenyl)-ethyl]-3,4-dihydro-1H-isoquinolin-2-yl}-phenyl-acetic acid methyl ester.

LC-MS: rt=0.88 min, 500 (M+1, ES+).

2. Synthesis of {6,7-dimethoxy-1-[2-(6-trifluoromethyl-pyridin-3-yl)-ethyl]-3,4-dihydro-1H-isoquinolin-2-yl}-phenyl-acetic acid

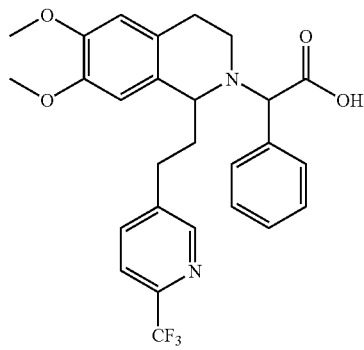

This compound is prepared by saponification of {6,7-dimethoxy-1-[2-(6-trifluoromethyl-pyridin-3-yl)-ethyl]-3,4-dihydro-1H-isoquinolin-2-yl}-phenyl-acetic acid methyl ester.
LC-MS: rt=1.18 min, 499 (M−1, ES−), 501 (M+1, ES+).

3. Synthesis of {(1S)-6,7-dimethoxy-1-[2-(4-trifluoromethyl-phenyl)-ethyl]-3,4-dihydro-1H-isoquinolin-2-yl}-phenyl-acetic acid

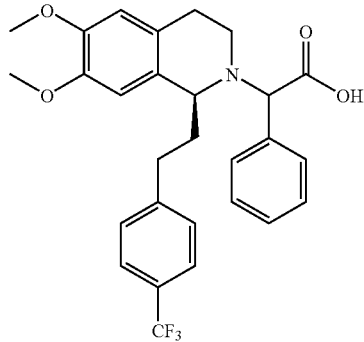

This compound is prepared by saponification of {(1S)-6,7-dimethoxy-1-[2-(4-trifluoromethyl-phenyl)-ethyl]-3,4-dihydro-1H-isoquinolin-2-yl}-phenyl-acetic acid methyl ester.
LC-MS: rt=0.88 min, 500 (M+1, ES+).

EXAMPLE 1

Synthesis of 2-{6,7-dimethoxy-1-[2-(4-trifluoromethyl-phenyl)-ethyl]-3,4-dihydro-1H-isoquinolin-2-yl}-N-methyl-2-phenyl-acetamide

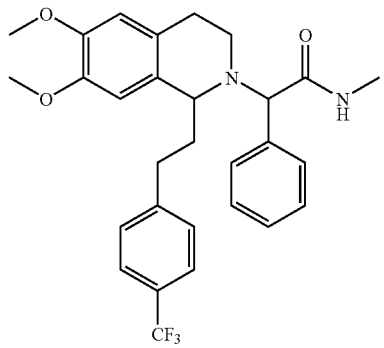

At 0° C. methylamine hydrochloride (15.0 mmol) and NaHCO$_3$ (20.0 mmol) are added to a solution of {6,7-dimethoxy-1-[2-(4-trifluoromethyl-phenyl)-ethyl]-3,4-dihydro-1H-isoquinolin-2-yl}-phenyl-acetic acid (10.0 mmol) in DMF (200 mL). After 15 min HOBt (12.0 mmol) and EDC hydrochloride (22.0 mmol) are added. The mixture is stirred for 10 min and kept for additional 14 h at 0° C. without stirring. Water (100 mL), EA (300 mL) and cyclohexane (100 mL) are added, the layers are separated and the aqueous layer is extracted twice with EA/cyclohexane 3:1 (2×150 mL). The combined organic extracts are washed with a sat. aqueous NaHCO$_3$ solution (100 mL) and brine (100 mL) and dried over Na$_2$SO$_4$. The solvents are removed in vacuo and the residue is purified by flash chromatography (gradient: EA/heptane 1/2 to EA/ethanol/heptane 2/1/2) to give the desired amides as mixture of all 4 possible stereoisomers.
LC-MS: rt=0.89 min, 513 (M+1, ES+).

EXAMPLE 2

Synthesis of (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide

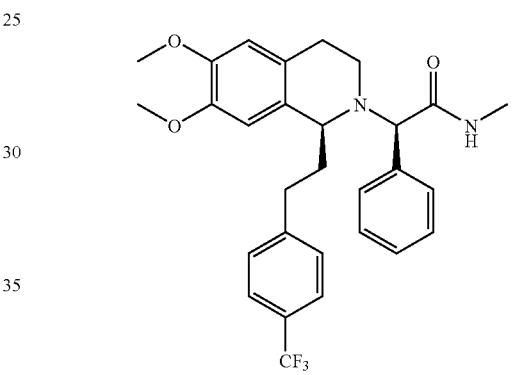

a) Procedure I (Via Amide-Coupling):

At 0° C. methylamine hydrochloride (23.7 mmol) and NaHCO$_3$ (2.01 g, 23.9 mmol) are added to a solution of {(1S)-6,7-dimethoxy-1-[2-(4-trifluoromethyl-phenyl)-ethyl]-3,4-dihydro-1H-isoquinolin-2-yl}-phenyl-acetic acid (21.5 mmol) in DMF (300 mL). After 5 min HOBt (23.8 mmol) and EDC hydrochloride (47.6 mmol) are added. The mixture is stirred for 2 h and kept for additional 14 h at 0° C. without stirring. Water (300 mL) and EA (300 mL) are added, the layers are separated and the aqueous layer is extracted three times with EA (3×150 mL). The combined organic extracts are washed with water (3×100 mL) and brine (100 mL). The solvents are removed in vacuo and the residue is purified by flash chromatography (EA/heptane 3/2) to give the desired amides as separated dia-stereoisomers.

b) Procedure II (Via Alkylation with a Bromide Derivative):

DIPEA (119 mmol) is added to a solution of 2-bromo-N-methyl-2-phenyl-acetamide (59.6 mmol) in THF (150 mL). A solution of (1S)-6,7-dimethoxy-1-[2-(4-trifluoromethyl-phenyl)-ethyl]-1,2,3,4-tetrahydroisoquinoline (62.7 mmol) in THF (200 mL) is added and the reaction mixture is stirred at 60° C. for 7 d. Ethyl acetate (200 mL) and a sat. aqueous solution of NaHCO$_3$ (200 mL) are added, the layers are separated and the aqueous layer is extracted twice with ethyl acetate (2×100 mL). The combined organic extracts are washed with water (3×50 mL), dried over MgSO$_4$ and concentrated in vacuo. The residue is purified by flash chromatography (ethyl acetate/heptane 3/2) to give the desired amides as separated diastereoisomers.

c) Procedure III (Via Alkylation with a Tosylate Derivative):

A solution of (1S)-6,7-dimethoxy-1-[2-(4-trifluoromethyl-phenyl)-ethyl]-1,2,3,4-tetrahydroisoquinoline (100 mg), toluene-4-sulfonic acid (S)-methylcarbamoyl-phenylmethyl ester (100 mg) and DIPEA (0.065 mL) in butanone (5.0 mL) is heated to reflux for 3 d and cooled to RT. Ethyl acetate is added and the mixture is washed with sat. aqueous $NaHCO_3$ solution and brine. The organic layer is dried over $Na_2SO_4$ and the solvents are removed in vacuo. THF (2.0 mL) and a solution of HCl in isopropanol (5-6 M, 0.10 mL) are added to the crude product and the solvents are removed in vacuo. The obtained solid is recrystallized from THF (2.0 mL) to give the desired amide as white crystals.

Datas are given for the free base of the more active diastereoisomer ($IC_{50}$, FLIPR).

$R_f$=0.21 (EA/heptane 2/1);

LC-MS: rt=0.90 min, 513 (M+1, ES+);

Chiral HPLC: rt=18.9 min (hexane/ethanol 95/5; diastereoisomer: rt=22.3 min; the two other possible stereoisomers with an opposite configuration in the 1,2,3,4-tetrahydroisoquinoline ring system are prepared in analogy to the synthesis described above using N-((1S,2S)-2-amino-1,2-diphenyl-ethyl)-2,4,6-trimethyl-benzene-sulfonamide (step G.2) for the transfer hydrogenation: these isomers have retention times of: rt=26.2 min, 33.8 min);

$^1$H-NMR (300 MHz, $CDCl_3$): δ=1.74-1.87 (m, 1H), 2.04-2.19 (m, 1H), 2.40-2.52 (m, 1H), 2.59-2.72 (m, 1H), 2.86 (d, J=4.8 Hz, 3H), 2.86-3.01 (m, 1H), 3.03-3.18 (m, 2H), 3.30-3.41 (m, 2H), 3.69 (s, 3H), 3.84 (s, 3H), 4.25 (s, 1H), 6.03 (s, 1H), 6.57 (s, 1H), 6.87 (q, J=4.8 Hz, 1H), 7.10-7.16 (m, 2H), 7.19-7.28 (m, 5H), 7.50 (d, J=8.1 Hz, 2H);

$^{13}$C-NMR (75 MHz, $CDCl_3$): δ=21.9, 26.1, 33.4, 37.8, 40.7, 55.8, 55.9, 57.0, 70.1, 110.0, 111.4, 124.2 (q, $J_{C,F}$=271 Hz), 124.9, 125.1 (q, $J_{C,F}$=4 Hz), 128.0 (q, $J_{C,F}$=32 Hz), 128.1, 128.4, 128.5, 129.0, 137.0, 146.2, 147.1, 147.6, 172.2.

EXAMPLE 3

Synthesis of 2-{6,7-dimethoxy-1-[2-(6-trifluoromethyl-pyridin-3-yl)-ethyl]-3,4-dihydro-1H-isoquinolin-2-yl}-N-methyl-2-phenyl-acetamide

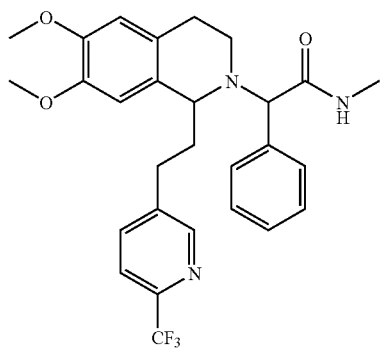

A mixture of {6,7-dimethoxy-1-[2-(6-trifluoromethyl-pyridin-3-yl)-ethyl]-3,4-dihydro-1H-isoquinolin-2-yl}-phenyl-acetic acid (0.20 mmol), methylamine hydrochloride (0.20 mmol), PyBOP (0.20 mmol) and DIPEA (0.46 mmol) in DMF (1.0 mL) is stirred at RT for 20 h. Water and EA are added, the layers are separated and the aqueous layer is extracted with EA. The combined organic extracts are dried over $MgSO_4$ and concentrated in vacuo. The residue is purified by flash chromatography (EA) to give the desired product as a viscous oil.

LC-MS: rt=1.17 min, 514 (M+1, ES+).

EXAMPLE 4

Synthesis of (2R)-2-{(1S)-6,7-dimethoxy-1-[2-(6-trifluoromethyl-pyridin-3-yl)-ethyl]-3,4-dihydro-1H-isoquinolin-2-yl}-N-methyl-2-phenyl-acetamide

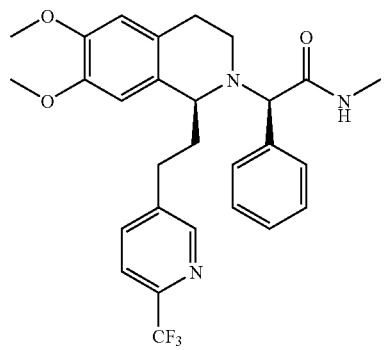

DIPEA (20.8 mmol) is added to a solution of (1S)-6,7-dimethoxy-1-[2-(6-trifluoromethyl-pyridin-3-yl)-ethyl]-1,2,3,4-tetrahydroisoquinoline (10.0 mmol) in THF (40 mL). 2-Bromo-N-methyl-2-phenyl-acetamide (10.4 mmol) is added and the mixture is stirred at 60° C. for 5 d. Water (100 mL) and ethyl acetate (200 mL) are added, the layers are separated and the aqueous layer is extracted twice with ethyl acetate (2×100 mL). The combined organic extracts are concentrated in vacuo and the residue is purified by flash chromatography (ethyl acetate/heptane 3/1) to give the desired amides as separated diastereoisomers.

Data are given for the more active diastereoisomer ($IC_{50}$, FLIPR).

$R_f$=0.15 (EA/heptane 3/1);

LC-MS: rt=0.81 min, 514 (M+1, ES+);

$^1$H-NMR (300 MHz, $CDCl_3$): δ=1.73-1.86 (m, 1H), 2.02-2.16 (m, 1H), 2.41-2.52 (m, 1H), 2.59-2.71 (m, 1H), 2.87 (d, J=5.1 Hz, 3H), 2.88-3.03 (m, 1H), 3.04-3.17 (m, 2H), 3.26-3.36 (m, 2H), 3.69 (s, 3H), 3.83 (s, 3H), 4.23 (s, 1H), 6.04 (s, 1H), 6.55 (s, 1H), 6.74 (q, J=5.1 Hz, 1H), 7.10-7.16 (m, 2H), 7.19-7.27 (m, 3H), 7.51-7.61 (m, 2H), 8.52 (s, 1H).

Biological Assays

In Vitro Assay

The orexin receptor antagonistic activity of the compounds of general formula (I) is determined in accordance with the following experimental method.

Experimental Method:

Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 μg/ml G418, 100 U/ml penicillin, 100 μg/ml streptomycin and 10% inactivated fetal calf serum (FCS). The cells are seeded at 80'000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in methanol:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 μl of loading medium (HBSS containing 1% FCS, 2 mM HEPES, 5 mM probenecid (Sigma) and 3 μM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 μl HBSS containing 2.5 mM probenecid, 0.1% BSA, 2 mM HEPES. 100 μl of that same buffer is left in each well.

Within the Fluorescent Imaging Plate Reader (FLIPR, Molecular Devices), antagonists are added to the plate in a volume of 50 μl, incubated for 20 min and finally 100 μl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. Antagonistic activities of compounds are in the nanomolar range.

Measurements of the Inhibitory Potency Against Different CYPs:

The CYP inhibition studies are performed using human liver microsomes (pool of 10 individuals), literature-established CYP isoform-selective substrates and quantification by either LC-MS/MS (for CYP3A4 and CYP2C9) or conventional HPLC with fluorimetric detection (for CYP2D6). The specific probes were midazolam 1'-hydroxylation for CYP3A4, dextromethorphan 3-hydroxylation for CYP2D6 and diclofenac 4'-hydroxylation for CYP2C9. Experiments were carried out in duplicate in 96-well plates with substrate concentrations around the respective $K_m$ values (Table 1 shows an overview of the experimental conditions) and 7 inhibitor concentrations up to 50 μM. Controls (sulfaphenazole for CYP2C9, fluoxetine for CYP2D6, and nicardipine for CYP3A4) were run in parallel in each plate.

TABLE 1

| CYP isoform | substrates and concentration (μM) | microsomal conc. (mg/ml) | incubation time (min) |
|---|---|---|---|
| CYP3A4 | midazolam (5) | 0.25 | 5 |
| CYP2C9 | diclofenac (5) | 0.10 | 6 |
| CYP2D6 | dextromethorphan (8) | 0.20 | 30 |

As illustrated in Table 2 hereinafter, compounds described in examples 1 to 4 show remarkably low affinities against CYP3A4.

TABLE 2

| Examples | CYP3A4 $IC_{50}$ [μM] |
|---|---|
| Example 1 | 32 |

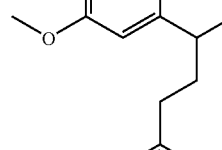

| | |
|---|---|
| Example 2 | 46 |

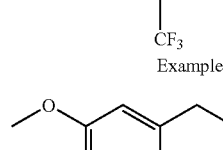

| | |
|---|---|
| Example 3 | 18 |

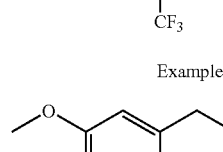

| | |
|---|---|
| Example 4 | 50 |

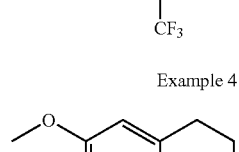

In Vivo Assay:

Spontaneous Home Cage Activity and Body Temperature Measured by Radiotelemetry in Laboratory Rats:

The objective of the present test is to record the circadian behavioral activity of rats after oral administration of a compound according to general formula (I) of the invention.

Decreased home cage activity measured by telemetry in male Wistar rats was considered as an indication for sleep-inducing potential of a restricted number of highly optimized 1,2,3,4-tetrahydroisoquinoline derivatives.

Psychotropic drugs such as antidepressants, antipsychotics, sleep inducers or psychostimulants are well known to reduce or enhance home cage activity and body temperature following oral administration to laboratory animals. Thermoregulation is a complex process that contributes to homeostasis by coordinating metabolism, energy balance and behaviour. Body temperature changes with circadian behavioural activity and increases when locomotion increases. These two parameters were measured by telemetry in conscious freely moving Wistar rats. Anaesthetized animals were implanted, under aseptic conditions, with a body temperature/activity telemetric device into the peritoneal cavity. More than two weeks after the implantation of the telemetry system, data were collected at 5 minutes intervals during 96 hours. Hourly means were calculated for each rat. The first 48 h were used as an internal control trace and drug effects were compared to vehicle placebo. This method is validated pharmacologically by measuring amplitude and time course of both hypoactivity and hypothermia induced by GABA-A receptor modulators such as zolpidem.

As illustrated in Table 3 hereinafter, administration of orexin receptor antagonists of the present invention such as those described in examples 1 to 4 are orally active.

TABLE 3

| Examples | p.o activity |
| --- | --- |
| Example 1 | yes |
| Example 2 | yes |
| Example 3 | yes |
| Example 4 | yes |

The invention claimed is:

1. The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide, structurally represented by formula (II):

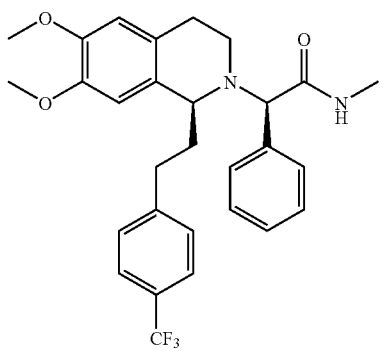

(II)

in free or pharmaceutically acceptable salt form.

2. The compound according to claim 1 which is (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide in free base form.

3. The compound according to claim 1 which is (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide in pharmaceutically acceptable acid addition salt form;

wherein the acidic component of the acid addition salt is selected from the group consisting of hydrochloric acid, hydrobromic acid, hydroiodic acid, sulfuric acid, phosphoric acid, nitric acid, citric acid, formic acid, acetic acid, maleic acid, tartaric acid, fumaric acid, benzoic acid, pamoic acid, stearic acid, methanesulfonic acid, p-toluenesulfonic acid, salicylic acid, succinic acid, and trifluoroacetic acid.

4. The compound according to claim 1 which is (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide hydrochloric acid salt.

5. A pharmaceutical composition comprising at least one compound according to any one of claims 1-4 and a pharmaceutically acceptable carrier material.

6. A method of preventing or treating insomnia comprising administering to a subject in need thereof an effective amount of the compound according to any one of claims 1-4.

* * * * *